US007033808B2

(12) United States Patent
Kizaki et al.

(10) Patent No.: US 7,033,808 B2
(45) Date of Patent: Apr. 25, 2006

(54) CARBONYL REDUCTASE, GENE THEREOF AND METHOD OF USING THE SAME

(75) Inventors: Noriyuki Kizaki, Moriguchi (JP); Yoshihiko Yasohara, Himeji (JP); Junzo Hasegawa, Akashi (JP)

(73) Assignee: Kaneka Corporation, Osaka (JP)

( * ) Notice: Subject to any disclaimer, the term of this patent is extended or adjusted under 35 U.S.C. 154(b) by 148 days.

(21) Appl. No.: 10/088,920

(22) PCT Filed: Aug. 1, 2001

(86) PCT No.: PCT/JP01/06619

§ 371 (c)(1),
(2), (4) Date: Jun. 3, 2002

(87) PCT Pub. No.: WO02/10399

PCT Pub. Date: Feb. 7, 2002

(65) Prior Publication Data

US 2003/0186412 A1    Oct. 2, 2003

(30) Foreign Application Priority Data

Aug. 1, 2000    (JP)    ............... 2000-232756

(51) Int. Cl.
C12N 9/02    (2006.01)
C12N 1/20    (2006.01)
C12N 15/00   (2006.01)
C12P 7/02    (2006.01)
C07H 21/04   (2006.01)

(52) U.S. Cl. ............... 435/189; 435/4; 435/6; 435/69.1; 435/71.1; 435/252.3; 435/320.1; 435/252.33; 435/155; 536/23.2; 536/23.7

(58) Field of Classification Search ............... 435/190, 435/440, 320.1, 325, 252.3, 6, 69.1, 26, 4, 435/189, 155, 71.1, 252.33; 536/23.2, 23.7
See application file for complete search history.

(56) References Cited

U.S. PATENT DOCUMENTS 4,096,331 A    6/1978    Boswell, Jr. et al.

FOREIGN PATENT DOCUMENTS

| EP | 0 942 068 A | 9/1999 |
|---|---|---|
| JP | 61-267577 | 11/1986 |
| JP | 6-141876 | 5/1994 |
| JP | 10-150998 | * 6/1998 |
| WO | WO 98/23768 | 6/1998 |
| WO | WO 98/23769 | 6/1998 |

OTHER PUBLICATIONS

Blattner et al. The complete genome sequence of *Escherichia coli* K-12. Science. Sep. 5, 1997;277 (5331):1453-74.*
Horiguchi et al., "Enzymatic Optical Resolution of N-Benzyl-3-pyrrolidinol," *Biosci. Biotech. Biochem.* (1995), vol. 59, No. 7. pp. 1287-1290, Japan Society for Bioscience, Biotechnology. and Agrochemistry.
Database Unit Prot Online, "OXIDOREDUCTASE", EBI Accession No. UNIPROT:Q67RQ0 (XP002311041), Oct. 25, 2004.

* cited by examiner

*Primary Examiner*—Manjunath Rao
*Assistant Examiner*—Yong Pak
(74) *Attorney, Agent, or Firm*—Foley & Lardner LLP

(57) ABSTRACT

The present invention provides a novel polypeptide producing (S)-N-benzyl-3-pyrrolidinol, a DNA coding for it and a method of using them.

A polypeptide having the following physicochemical properties (1) to (5):
(1) Action: It asymmetrically reduces N-benzyl-3-pyrrolidinone to produce (S)-N-benzyl-3-pyrrolidinol with NADPH as a coenzyme;
(2) Optimum action pH: 4.5 to 5.5;

(3) Optimum action temperature: 40° C. to 45° C.;
(4) Molecular weight: About 29,000 as determined by gel filtration analysis, about 35,000 as determined by SDS-polyacrylamide gel electrophoresis analysis;
(5) Inhibitor: It is inhibited by the divalent copper ion.

Further, a polypeptide having the amino acid sequence shown under SEQ ID NO:1 in the sequence listing; or a polypeptide having an amino acid sequence obtainable from the amino acid sequence shown under SEQ ID NO:1 in the sequence listing by substitution, insertion, deletion and/or addition of one or more amino acids and having enzyme activity in asymmetrically reducing N-benzyl-3-pyrrolidinone to produce (S)-N-benzyl-3-pyrrolidinol.

19 Claims, 2 Drawing Sheets

Fig 1.

```
   1 GGTACCCGCCGCCCTCCTATAAGCCAGCACCGGTCGAGGACGCGCCGGCCCTTCGAGGAT   61
  61 CTCAGCCCACGTCCCGCCTCAGGACAACCAGAAGGAAGTGATCGCGGATGCGACGGATGA  121
                                                       M  R  R  M  T
 121 CGCTGCCGAGTGGGGAGTCCATCCCTGTGCTGGGCCAGGGCACCTGGGGCTGGGGTGAGG  181
      L  P  S  G  E  S  I  P  V  L  G  Q  G  T  W  G  W  G  E  D
 181 ACCCCGGCCGCCGCGGCGACGAGGTCGCCGCGCTGCACGCCGGCCTCGAGCTGGGCATGA  241
      P  G  R  R  G  D  E  V  A  A  L  H  A  G  L  E  L  G  M  T
 241 CGCTGGTCGACACCGCCGAGATGTACGCCGACGGCGGTGCGGAGGAGGTGGCTGGTGAAG  301
      L  V  D  T  A  E  M  Y  A  D  G  G  A  E  E  V  A  G  E  A
 301 CATTGGCGGGTCGCCGCGACGAGGCGTTCGTGGTCAGCAAGGTCATGCCGTCCCACGCCT  361
      L  A  G  R  R  D  E  A  F  V  V  S  K  V  M  P  S  H  A  S
 361 CCCGTTCCGGCACGATCGCGGCCTGCGAACGCAGCCTGAAACGCCTGGGCACCGATCGGA  421
      R  S  G  T  I  A  A  C  E  R  S  L  K  R  L  G  T  D  R  I
 421 TCGACCTCTACCTGCTGCACTGGCAGGGCAGGTACCCGCTGCAGGACACCGTCGCGGCCT  481
      D  L  Y  L  L  H  W  Q  G  R  Y  P  L  Q  D  T  V  A  A  F
 481 TCCACCAGCTCGTCGAGGACGGGAAAATCCGATACTGGGGCGTCAGCAACTTCGACCACC  541
      H  Q  L  V  E  D  G  K  I  R  Y  W  G  V  S  N  F  D  H  R
 541 GGGCCCTCGCCGAGCTGCAGGACGTGCCGGGCACCAGCGGGCTGACCACGGATCAGGTGC  601
      A  L  A  E  L  Q  D  V  P  G  T  S  G  L  T  T  D  Q  V  L
 601 TGTACAACCTGTCGCGGCGAGGACCGGAGTACGACCTGCTGCCGTGGTGCGCCGACCACC  661
      Y  N  L  S  R  R  G  P  E  Y  D  L  L  P  W  C  A  D  H  Q
 661 AGCTGCCGGTCATGGCGTACTCGCCGATCGAGCAGGGCCGCATCCTTGACGACACGACGC  721
      L  P  V  M  A  Y  S  P  I  E  Q  G  R  I  L  D  D  T  T  L
 721 TGAACGACGTCGCGGCCCGTCACAGCGTCAGCCCCGCGGCGGCGGCCCTTGCCTGGGTGC  781
      N  D  V  A  A  R  H  S  V  S  P  A  A  A  A  L  A  W  V  L
 781 TGCGCCGCGACTCGCTCTGCACGATCCCCAAGGCGAGCAGCCCGCAGCACGTGCGCGACA  841
      R  R  D  S  L  C  T  I  P  K  A  S  S  P  Q  H  V  R  D  N
 841 ACGCCACAGCACTGGACGTGGAGCTGACCCGCGAAGACCTGGATGCTCTGGACCGTGCGT  901
      A  T  A  L  D  V  E  L  T  R  E  D  L  D  A  L  D  R  A  F
 901 TTCCGCCCCCGAGCGGACCGCGACCACTGGAAATGCTGTGACCCTGCCCCAGGGCGCAGC  961
      P  P  P  S  G  P  R  P  L  E  M  L  *
 961 CCGGTCGGTCCGGGCGGTCCGGGCAGTCCGGGCAGCGCTCCGGTCAGCGCAAGTCTCCGA 1021
1021 AGGACCTGCCTGTCACCTCCTCCTGAACCTGTGCACGCCATCCATCGACTCCTTTCCTCG 1081
1081 AGCCCTGTCGGGTTCGCGGTAGGCGCTGATCATCCGCTGGCAGGTCCCCCAAGTGCCCTC 1141
1141 GAGCCGGCCCTCTGCTTGTCGGTGAGCAACCCGGTTCCGGCGTGCAGGGTTCGACGGGC  1201
1201 GGAGTAGAGCGGGTCGCCCGTGCGGCCGCGGTGGCCATGCAGGTCCTGCTGGACCCGGCG 1261
1261 GTGGCAGCGGACCAACGCGTCGCCGGCTAACCGGACTGCGAGCGACCGGCGTTGTGGACG 1321
1321 CAGACGACCTGGACACTGGGCCGTGCCGTCAGGAGGATCTCCAAAGTCGGCGGCGGGCGT 1381
1381 TCAGGCGATGTCGAGGAAGGAACGGAGCTC                              1410
```

CARBONYL REDUCTASE, GENE THEREOF AND METHOD OF USING THE SAME

TECHNICAL FIELD

The present invention relates to a novel polypeptide, a gene coding for the polypeptide, an expression vector for the expression of the polypeptide, a transformant obtained by transformation of a host using the expression vector, and a production method of a compound useful as a material for the synthesis of medicinal and other compounds using the above transformant.

In more detail, the invention relates to a polypeptide isolated from a microorganism having enzyme activity in asymmetrically reducing N-benzyl-3-pyrrolidinone to produce (S)-N-benzyl-3-pyrrolidinol and having such enzyme activity, a DNA coding for the polypeptide, an expression vector containing the DNA, and a transformant obtained by transformation using the expression vector. The present invention also relates to a production method of (S)-N-benzyl-3-pyrrolidinol.

(S)-N-Benzyl-3-pyrrolidinol is a compound useful as an intermediate for the synthesis of medicinal compounds such as β-lactam antibiotics and dihydropyridine compounds.

BACKGROUND ART

Known as the production method of optically active (S)-N-benzyl-3-pyrrolidinol are the method which comprises synthesizing from an optically active compound and the method which comprises carrying out asymmetric synthesis or optical resolution starting with a prochiral compound. As such a method, JP-A-06-141876 discloses a production method of optically active N-benzyl-3-pyrrolidinol which comprises stereoselectively reducing N-benzyl-3-pyrrolidinone in the presence of an enzyme having activity in stereoselectively reducing this N-benzyl-3-pyrrolidinone. Further, JP-A-10-150997 discloses a production method of optically active N-benzyl-3-pyrrolidinol which comprises treating N-benzyl-3-pyrrolidinone with a cell or a culture of a microorganism or a treated product thereof. However, these methods are low in attainable substrate concentration and in conversion from the substrate to the product, hence cannot be put to practical use.

SUMMARY OF THE INVENTION

The present inventors found a microorganism-derived polypeptide which asymmetrically reduces N-benzyl-3-pyrrolidinone to produce (S)-N-benzyl-3-pyrrolidinol and found that (S)-N-benzyl-3-pyrrolidinol can be produced efficiently, and have now completed the present invention.

It is an object of the present invention to provide a polypeptide capable of asymmetrically reducing N-benzyl-3-pyrrolidinone to produce (S)-N-benzyl-3-pyrrolidinol. Another object of the invention is to produce that polypeptide efficiently utilizing the gene recombination technology. A further object of the invention is to provide a transformant capable of simultaneously producing, at high levels, that polypeptide and a polypeptide having glucose dehydrogenase activity and, further, provide a practical production method of (S)-N-benzyl-3-pyrrolidinol using that transformant.

Thus, the present invention comprises a polypeptide having the following physicochemical properties (1) to (5):
(1) Action: It asymmetrically reduces N-benzyl-3-pyrrolidinone to produce (S)-N-benzyl-3-pyrrolidinol with NADPH as a coenzyme;
(2) Optimum action pH: 4.5 to 5.5;
(3) Optimum action temperature: 40° C. to 45° C.;
(4) Molecular weight: About 29,000 as determined by gel filtration analysis, about 35,000 as determined by SDS-polyacrylamide gel electrophoresis analysis;
(5) Inhibitor: It is inhibited by the divalent copper ion.

Further, the present invention is a polypeptide described in the following (a) or (b):
(a) A polypeptide having the amino acid sequence shown under SEQ ID NO:1 in the sequence listing;
(b) A polypeptide having an amino acid sequence obtainable from the amino acid sequence shown under SEQ ID NO:1 in the sequence listing by substitution, insertion, deletion and/or addition of one or more amino acids and having enzyme activity in asymmetrically reducing N-benzyl-3-pyrrolidinone to produce (S)-N-benzyl-3-pyrrolidinol.

Furthermore, the present invention comprises DNAs coding for these polypeptides. Or, it also comprises a DNA coding for a polypeptide having enzyme activity in asymmetrically reducing N-benzyl-3-pyrrolidinone to produce (S)-N-benzyl-3-pyrrolidinol, and hybridizing with a DNA having a nucleotide sequence shown under SEQ ID NO:2 in the sequence listing under stringent conditions, or a DNA coding for a polypeptide having enzyme activity in asymmetrically reducing N-benzyl-3-pyrrolidinone to produce (S)-N-benzyl-3-pyrrolidinol, and having at least 60% sequence identity with a nucleotide sequence shown under SEQ ID NO:2 in the sequence listing.

Furthermore, it comprises an expression vector containing any of these DNAs and a transformant containing such expression vector.

The present invention also comprises a production method of (S)-N-benzyl-3-pyrrolidinol comprising
a step of reacting such transformant and/or a treated product thereof with N-benzyl-3-pyrrolidinone, and
a step of harvesting the thus-produced (S)-N-benzyl-3-pyrrolidinol.

DETAILED DISCLOSURE OF THE INVENTION

In the following, the present invention is described in detail.

First, the polypeptide of the invention is described.

The polypeptide of the invention has enzyme activity in asymmetrically reducing N-benzyl-3-pyrrolidinone represented by the formula (I) shown below to produce (S)-N-benzyl-3-pyrrolidinol represented by the formula (II) shown below.

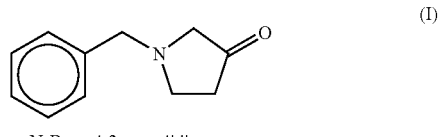

N-Benzyl-3-pyrrolidinone

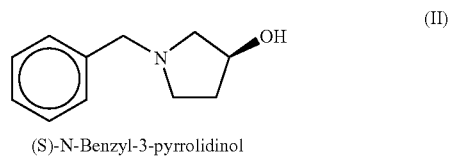

(S)-N-Benzyl-3-pyrrolidinol

As such polypeptide, there may be mentioned an enzyme having the following physicochemical properties (1) to (5).

(1) Action: It asymmetrically reduces N-benzyl-3-pyrrolidinone to produce (S)-N-benzyl-3-pyrrolidinol with NADPH as a coenzyme;
(2) Optimum action pH: 4.5 to 5.5;
(3) Optimum action temperature: 40° C. to 45° C.;
(4) Molecular weight: About 29,000 as determined by gel filtration analysis, about 35,000 as determined by SDS-polyacrylamide gel electrophoresis analysis;
(5) Inhibitor: It is inhibited by the divalent copper ion.

In the present invention, the enzyme activity of the polypeptide is determined by adding the substrate N-benzyl-3-pyrrolidinone (1 mM), the coenzyme NADPH (0.167 mM) and the enzyme to 100 mM phosphate buffer (pH 6.5) and measuring the decrease in absorbance at the wavelength 340 nm at 30° C.

The optimum action pH and optimum action temperature of the peptide are determined, for example by varying the reaction pH or reaction temperature in the above reducing activity measurement system and measuring the reducing activity.

The gel filtration analysis-based molecular weight of the peptide is determined by calculation from the elution time relative to those of reference proteins in gel filtration. The SDS-polyacrylamide gel electrophoresis-based molecular weight is determined by calculation from the mobility relative to those of reference proteins in SDS-polyacrylamide gel electrophoresis.

The inhibitors are determined, for example by adding various compounds to the above reducing activity measurement system and measuring the reducing activity of each compound.

The polypeptide of the invention can be obtained from a microorganism having an activity in asymmetrically reducing N-benzyl-3-pyrrolidinone to produce (S)-N-benzyl-3-pyrrolidinol. Thus, the microorganism to be used as the source of the polypeptide is not particularly restricted but includes, for example, microorganisms belonging to the genus *Micrococcus*, among which the strain *Micrococcus luteus* IFO 13867 is particularly preferred. The microorganism producing the polypeptide of the invention may be a wild strain or a mutant. Or, a microorganism obtainable by cell fusion or by such a genetic method as gene manipulation may also be used. A gene manipulated microorganism capable of producing the polypeptide of the invention can be obtained by a method comprising a step of isolating and/or purifying such enzyme and determining a part or the whole of the amino acid sequence thereof, a step of determining a nucleotide sequence coding for the enzyme based on that amino acid sequence, a step of obtaining a nucleotide sequence coding for the enzyme based on that amino acid sequence, and a step of obtaining a recombinant microorganism by introducing that nucleotide sequence into another microorganism.

As for the culture medium for the microorganism producing the polypeptide of the invention, ordinary liquid culture medium containing carbon sources, nitrogen sources, inorganic salts, organic nutrients and so on can be used provided that the microorganism can grow thereon.

The term "culture of the microorganism" as used in this specification means cells of the microorganism or a culture fluid containing such cells. The "treated product thereof" means an extract or purified product obtained from the cells of the microorganism or a culture fluid containing such cells by extraction, purification or some other treatment.

The polypeptide of the invention can be purified from the microorganism producing that polypeptide in the conventional manner. For example, cells of the microorganism are cultured on an appropriate medium, and cells are harvested from the culture fluid by centrifugation. The cells obtained are disrupted using a sonicator, for instance, and the cell residue is removed by centrifugation to give a cell-free extract. The polypeptide can be purified from this cell-free extract by applying, singly or in combination, such techniques as salting out (e.g. ammonium sulfate precipitation, sodium phosphate precipitation), solvent precipitation (protein fractionation precipitation using acetone, ethanol or the like), dialysis, gel filtration, ion exchange, column chromatography such as reversed phase and ultrafiltration.

The polypeptide of the invention may be a natural enzyme obtained from a microorganism as mentioned above or may be a recombinant enzyme. As a natural enzyme, there may be mentioned a polypeptide having the amino acid sequence shown under SEQ ID NO:1 in the sequence listing.

The polypeptide of the invention may also be a polypeptide having an amino acid sequence obtainable from the amino acid sequence shown under SEQ ID NO:1 in the sequence listing by substitution, insertion, deletion and/or addition of one or more amino acids and having enzyme activity in asymmetrically reducing N-benzyl-3-pyrrolidinone to produce (S)-N-benzyl-3-pyrrolidinol.

Such polypeptide can be prepared from the polypeptide having the amino acid sequence shown under SEQ ID NO:1 in the sequence listing by such a known method as described in Current Protocols in Molecular Biology (John Wiley and Sons, Inc., 1989).

The phrase "having enzyme activity in asymmetrically reducing N-benzyl-3-pyrrolidinone to produce (S)-N-benzyl-3-pyrrolidinol" is used herein to indicate that when the polypeptide in question is subjected to reaction with N-benzyl-3-pyrrolidinone under the above-mentioned reducing activity measurement conditions, (S)-N-benzyl-3-pyrrolidinol is produced in a yield not less than 10%, preferably not less than 40%, more preferably not less than 60%, as compared with the case where the polypeptide having the amino acid sequence shown under SEQ ID NO:1 in the sequence listing is used.

The DNA of the invention is described in the following.

The DNA of the invention may be any DNA coding for such a polypeptide as mentioned above. It may be a DNA having the nucleotide sequence shown under SEQ ID NO:2 in the sequence listing, or a DNA coding for a polypeptide having enzyme activity in asymmetrically reducing N-benzyl-3-pyrrolidinone to produce (S)-N-benzyl-3-pyrrolidinol, and hybridizing with the DNA having the nucleotide sequence shown under SEQ ID NO:2 in the sequence listing under stringent conditions.

The term "DNA hybridizing with the DNA having the nucleotide sequence shown under SEQ ID NO:2 in the sequence listing under stringent conditions" means a DNA obtainable by the technique of colony hybridization, plaque hybridization or southern hybridization, using the DNA having the nucleotide sequence shown under SEQ ID NO:2 in the sequence listing as a probe. More specifically, there may be mentioned a DNA identified by carrying out hybridization using a filter with the colony or plaque-derived DNA immobilized thereon, at 65° C. in the presence of 0.7 to 1.0 M NaCl, and then washing the filter with a 0.1- to 2-fold concentrated SSC solution (1-fold concentrated SSC solution comprising 150 mm sodium chloride and 15 mM sodium citrate) at 65° C.

The hybridization can be carried out according to the method described in Molecular Cloning, A laboratory manual, second edition (Cold Spring Harbor Laboratory Press, 1989) or elsewhere.

The DNA of the invention may be a DNA coding for a polypeptide having enzyme activity in asymmetrically reducing N-benzyl-3-pyrrolidinone to produce (S)-N-benzyl-3-pyrrolidinol and having at least 60% sequence identity, preferably at least 80% sequence identity, more preferably at least 90% sequence identity, still more preferably at least 95% sequence identity, most preferably at least 99% sequence identity, with the nucleotide sequence shown under SEQ ID NO:2 in the sequence listing.

The term "sequence identity" means that the two nucleotide sequences under comparison are identical with each other, and the percentage (%) of sequence identity between two nucleotide sequences under comparison is calculated by optimally arranging the two nucleotide sequences under comparison, counting those positions at which the same nucleotide (e.g. A, T, C, G, U or I) appears in both the sequences, dividing the thus-found number of conforming positions by the total number of bases under comparison and multiplying the quotient by 100. The sequence identity can be calculated using the following tools for sequence analysis: Unix Base GCG Wisconsin Package (Program Manual for the Wisconsin Package, Version 8, Sep. 1994, Genetics Computer Group, 575 Science Drive Madison, Wis., USA 53711; Rice, P. (1996) Program Manual for EGCG Package, Peter Rice, The Sanger Centre, Hinxton Hall, Cambridge, CB10 1RQ, England) and the ExPASy World Wide Web Molecular Biology Server (Geneva University Hospital and University of Geneva, Geneva, Switzerland).

The DNA of the invention can be obtained from a microorganism having enzyme activity in asymmetrically reducing N-benzyl-3-pyrrolidinone to produce (S)-N-benzyl-3-pyrrolidinol. As the microorganism, there may be mentioned, for example, microorganisms belonging to the genus *Micrococcus* and, as a particularly preferred strain, there may be mentioned the strain *Micrococcus luteus* IFO 13867.

In the following, an embodiment of the method of obtaining the DNA of the invention from a microorganism having enzyme activity in asymmetrically reducing N-benzyl-3-pyrrolidinone to produce (S)-N-benzyl-3-pyrrolidinol is described.

First, partial amino acid sequence of the purified polypeptide and of peptide fragments obtainable by digestion of that polypeptide with an appropriate endopeptidase are determined by the Edman technique. DNA primers are synthesized based on the thus-obtained amino acid sequence information. Then, the chromosomal DNA of the microorganism is prepared from that microorganism, which is the source of the above DNA, by a conventional method of DNA isolation, for example by the method of Murray et al. (Nucl., Acids Res. 8:4321–4325 (1980)). Using the above DNA primers, PCR is carried out with the chromosomal DNA as the template to amplify part of the polypeptide gene. Further, DNA probes are prepared by labeling part of the thus-amplified polypeptide gene by conventional methods, for example by the random primer labeling method (Anal. Biochem., 132, 6 (1983)). The chromosomal DNA of the microorganism is cleaved with an appropriate restriction enzyme, the restriction enzyme cleaved fragments are inserted into a vector and the resulting vectors are introduced into appropriate host cells to thereby construct a DNA library of the microbial chromosome. Screening of this DNA library is carried out by the colony hybridization, plaque hybridization or like method using the above DNA probes, whereby a DNA containing the polypeptide gene can be obtained. The nucleotide sequence of the thus-obtained DNA fragment containing the polypeptide gene can be determined by the dideoxy sequencing method or dideoxy chain termination method, or the like. For example, this can be carried out using the ABI PRISM Dye Terminator Cycle Sequencing Ready Reaction Kit (product of Perkin-Elmer) and the ABI 373A DNA Sequencer (product of Perkin-Elmer).

The expression vector and transformant of the present invention are now described.

The enzyme gene can be expressed in the transformant which is obtainable by inserting the DNA of the present invention to a vector and introducing the vector into a host. The vector to be used for this purpose may be any of those capable of expressing the enzyme gene in appropriate hosts. As such vector, there may be mentioned, for example, a plasmid vector, phage vector, cosmid vector, etc. It may be a shuttle vector capable of gene exchange between different host strains. Generally, such vector comprises such a regulatory factor as the lac UV5 promoter, trp promoter, trc promoter, tac promoter, lpp promoter, tuf B promoter, rec A promoter or pL promoter, and is suitably used as an expression vector containing an expression unit operatively connected to the DNA of the invention.

The term "regulatory factor" as used herein means a functional promoter and a nucleotide sequence having arbitrary related transcription elements (e.g. enhancer, CCAAT box, TATA box, SPI site, etc.).

The term "operatively connected" as used herein means that the DNA and various regulatory elements, such as promoter and enhancer, which regulate the expression thereof are joined together each in a state operative in a host so that the gene can be expressed. It is well known to the artisan that the type and species of the regulatory factor may vary according to the host.

As the host into which an expression vector containing the DNA of the invention is to be introduced, there may be mentioned bacteria, yeasts, filamentous fungi, plant cells and animal cells, for instance. *Escherichia coli* is preferred, however. The DNA of the invention can be introduced into a host in the conventional manner. When *Escherichia coli* is used as the host, the DNA of the invention can be introduced into the same by the calcium chloride method, for instance.

For producing (S)-N-benzyl-3-pyrrolidinol by asymmetrically reducing N-benzyl-3-pyrrolidinone using the DNA of the invention, a coenzyme such as NAPDH or NADH is required. However, by carrying out the reaction using an enzyme capable of converting the coenzyme oxidized to its reduced form (hereinafter referred to as coenzyme regenerating ability) together with a substrate thereof, namely combining a coenzyme regeneration system with the polypeptide of the invention, it is possible to markedly reduce the consumption of the coenzyme, which is expensive. Usable as the enzyme having coenzyme regenerating ability are, for example, hydrogenase, formate dehydrogenase, alcohol dehydrogenase, aldehyde dehydrogenase, glucose-6-phosphate dehydrogenase and glucose dehydrogenase. Glucose dehydrogenase is suitably used.

When a transformant containing both the DNA of the invention and a DNA coding for a polypeptide having glucose dehydrogenase activity is used, the above reaction can be carried out efficiently without separately preparing an enzyme having coenzyme regenerating ability and adding the same to the reaction system, although such reaction may also be carried out by adding a coenzyme regeneration system to the asymmetric reduction reaction system. Such transformant can be obtained by inserting the DNA of the invention and a DNA coding for a polypeptide having glucose dehydrogenase activity into the same vector and introducing this into a host, or by inserting these two DNAs respectively into two different vectors belonging to incompatible groups and introducing these into the same host. Thus, a transformant containing an expression vector comprising the DNA of the invention and the DNA coding for a polypeptide having glucose dehydrogenase activity, or a transformant containing both a first expression vector containing the DNA of the invention and an expression vector containing the DNA coding for a polypeptide having glucose dehydrogenase activity can be used. As for the polypeptide having glucose dehydrogenase activity, *Bacillus megaterium*-derived one is preferred.

The glucose dehydrogenase activity in the transformant is determined by adding the substrate glucose (0.1 M), the coenzyme NADP (2 mM) and the enzyme to 1 M Tris hydrochloride buffer (pH 8.0) and measuring the increase in absorbance at the wavelength 340 nm at 25° C.

Now, a production of (S)-N-benzyl-3-pyrrolidinol using the transformant of the invention is described.

Such production method comprises a step of reacting the above transformant and/or a treated product thereof with N-benzyl-3-pyrrolidinone and a step of harvesting the thus-produced (S)-N-benzyl-3-pyrrolidinol.

In the following, this method is more specifically described. First, the substrate N-benzyl-3-pyrrolidinone, NADPH or a like coenzyme, and a culture of the above transformant and/or a treated product thereof, are added to an appropriate solvent, and the reaction is allowed to proceed under stirring with the pH adjusted. This reaction is carried out at a temperature of 10° C. to 70° C., and the pH is maintained at 4 to 10 during the reaction. The reaction can be carried out batchwise or continuously. In the batchwise, the reaction substrate is added to a charge concentration of 0.1% to 70% (w/v). The treated product of the transformant so referred to herein means, for example, a crude extract, cultured cells, lyophilized organism bodies, acetone-dried organism bodies, a disruption product derived therefrom and the like. Further, these can be used in the form of the enzyme itself or cells as such immobilized by known means. This reaction is preferably carried out in the presence of a coenzyme regeneration system. For example, when, in carrying out this reaction, a transformant capable of producing both the polypeptide of the invention and glucose dehydrogenase is used, it is made possible to markedly reduce the consumption of the coenzyme by further adding glucose to the reaction system.

The (S)-N-benzyl-3-pyrrolidinol produced by the reaction can be harvested by a conventional method. For example, the suspended matter, such as cells, is removed, if necessary, by such treatment as centrifugation or filtration, the reaction solution is made basic by addition of sodium hydroxide or the like and extracted with an organic solvent such as ethyl acetate or toluene, and the organic solvent is then removed under reduced pressure. The product can be purified by further treatment such as distillation or chromatography and so on.

N-Benzyl-3-pyrrolidinone, which is to serve as the substrate in the reaction, can be prepared, for example, by the method described in JP-A-54-16466.

The quantities of N-benzyl-3-pyrrolidinone and (S)-N-benzyl-3-pyrrolidinol can be determined by gas chromatography (column: Uniport B 10% PEG-20M (3.0 mm ID×1.0 m), column temperature: 200° C., carrier gas: nitrogen, detection: FID). The optical purity of (S)-N-benzyl-3-pyrrolidinol can be measured by high performance liquid chromatography (column: Chiralcel OB (product of Daicel Chemical Industries), eluent: n-hexane/isopropanol/diethylamine=950/50/1,flow rate: 1 ml/min, detection: 254 nm).

Thus, according to the present invention, it is possible to efficiently produce the polypeptide included in the present invention and, by utilizing the same, an advantageous, production method of (S)-N-benzyl-3-pyrrolidinol is provided.

BRIEF DESCRIPTION OF THE DRAWINGS

FIG. 1 is a chart of the nucleotide sequence (SEQ ID NO: 2) of the DNA as determined in Example 3 and the amino acid sequence (SEQ ID NO: 1) deduced therefrom.

BEST MODES FOR CARRYING OUT THE INVENTION

Figure 2:
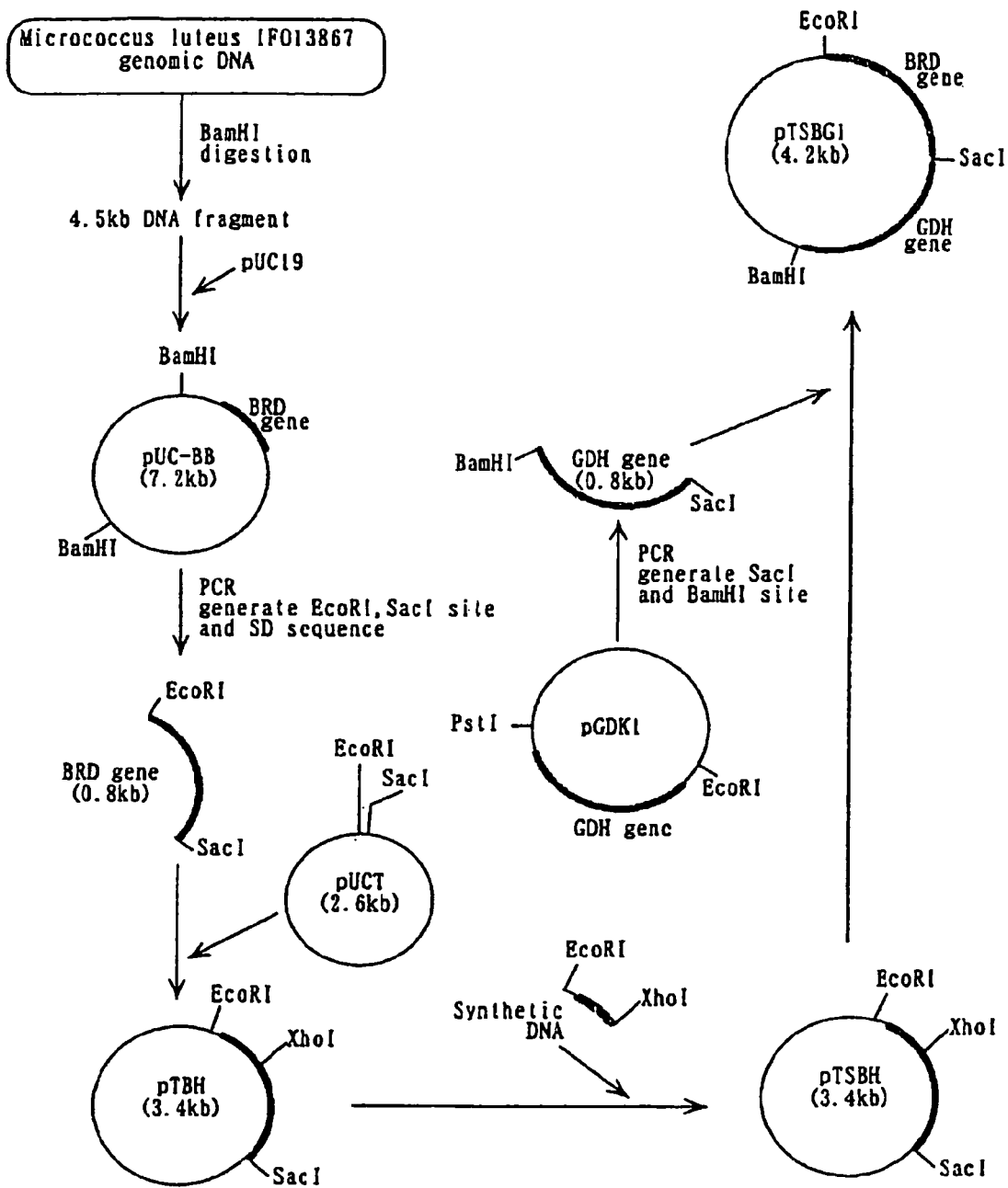
FIG. 2 is a chart of the method of constructing the recombinant plasmid pTSBG1 of Example 7 and the structure thereof.

The following Examples illustrate the present invention in detail. They are, however, by no means limitative of the scope of the present invention.

Detailed procedures and so on concerning the recombinant DNA technology used in the following Examples are described in the following literatures.

Molecular Cloning, 2nd Edition (Cold Spring Harbor Laboratory Press, 1989);

Current Protocols in Molecular Biology (Greene Publishing Associates and Wiley-Interscience).

EXAMPLE 1

Purification of Enzyme

An enzyme having the activity in asymmetrically reducing N-benzyl-3-pyrrolidinone to produce (S)-N-benzyl-3-pyrrolidinol was uniformly purified from the strain *Micrococcus luteus* IFO 13867 in the following manner.

(Cultivation of the Strain *Micrococcus luteus* IFO 13867)

A liquid medium (400 mL) having the following composition was prepared in each 2-L Sakaguchi flask and steam-sterilized at 120° C. for 20 minutes.

| Medium composition: | |
|---|---|
| Trypton | 1.6% (w/v) |
| Yeast extract | 1.0% (w/v) |
| NaCl | 0.5% (w/v) |
| Tap water | |
| pH 7.0 | |

This medium was inoculated with 1 ml of a culture fluid of the strain *Micrococcus luteus* IFO 13867 prepared in advance by preculture in the same medium, and shake culture was carried out at 30° C. for 50 hours.

(Preparation of Cell-free Extract)

Cells were collected by centrifugation from the above culture fluid (2 L) and washed with physiological saline. Thus, 42 g of wet cells of the above strain were obtained. These wet cells were suspended in 170 mL of 100 mM phosphate buffer (pH 7.0), then 2-mercaptoethanol and phenylmethylsulfonyl fluoride were added to respective final concentrations of 5 mM and 0.1 mM, and the cells were ultrasonically disrupted using SONIFIRE 250 (product of BRANSON). The cell residues were removed from the disrupted cell disruption by centrifugation, whereby 180 mL of a cell-free extract was obtained.

(Ammonium Sulfate Fractionation)

Ammonium sulfate was added to and dissolved in the cell-free extract obtained in the above manner to attain 40% saturation and the resulting precipitate was removed by centrifugation (during this procedure, the pH of the cell-free extract was maintained at 7.0 using aqueous ammonia). While the pH was maintained at 7.0 in the same manner as in the above procedure, ammonium sulfate was further added to and dissolved in this centrifugation supernatant to attain 65% saturation, and the resulting precipitate was collected by centrifugation. This precipitate was dissolved in 10 mM phosphate buffer (pH 7.0) containing 5 mM 2-mercaptoethanol, and the solution was dialyzed overnight using the same buffer.

(Phenyl Sepharose Column Chromatography)

Ammonium sulfate was dissolved in the crude enzyme solution obtained in the above manner to a final concentration of 1 M (while the pH of the crude enzyme solution was maintained at 7.0 using aqueous ammonia), and the solution was applied to a Phenyl sepharose CL-4B (product of Pharmacia Biotech) column (130 mL) equilibrated in advance with 10 mM phosphate buffer (pH 7.0) containing 5 mM 2-mercaptoethanol and 1 M ammonium sulfate so as to adsorb the enzyme. After washing the column with the same buffer, the active fraction was eluted with a linear gradient of ammonium sulfate (from 1 M to 0 M). The active fraction was collected and dialyzed overnight using 10 mM phosphate buffer (pH 7.0) containing 5 mM 2-mercaptoethanol.

(DEAE Sepharose Column Chromatography)

The crude enzyme solution obtained in the above manner was applied to a DEAE sepharose CL-4B (product of Pharmacia Biotech) column (20 mL) equilibrated in advance with 10 mM phosphate buffer (pH 7.0) containing 5 mM 2-mercaptoethanol so as to adsorb the enzyme. After washing the column with the same buffer, the active fraction was eluted with a linear gradient of NaCl (from 0 M to 1.0 M). The active fraction was collected and dialyzed overnight using 10 mM phosphate buffer (pH 7.0) containing 5 mM 2-mercaptoethanol.

(Blue Sepharose Column Chromatography)

The crude enzyme solution obtained in the above manner was applied to a Blue Sepharose CL-6B (product of Pharmacia Biotech) column (10 ml) equilibrated in advance with 20 mM phosphate buffer (pH 6.0) containing 5 mM 2-mercaptoethanol so as to adsorb the enzyme. After washing the column with the same buffer, the active fraction was eluted with a linear gradient of NaCl (from 0 M to 0.5 M). The active fraction was collected and dialyzed overnight using 10 mM phosphate buffer (pH 7.0) containing 5 mM 2-mercaptoethanol.

(Gel Filtration)

The crude enzyme solution obtained in the above manner was applied to a TSK-GEL G3000 SWXL column (product of Tosoh) equilibrated in advance with 100 mM phosphate buffer (pH 7.0) containing 5 mM 2-mercaptoethanol and 100 mM sodium sulfate, and the active fraction was eluted with the same buffer. The active fraction was collected and dialyzed overnight using 10 mM phosphate buffer (pH 7.0) containing 5 mM 2-mercaptoethanol to give an electrophoretically uniform, purified enzyme preparation. Hereinafter, this enzyme is referred to as BRD.

EXAMPLE 2

Measurements of Enzyme Properties

The enzyme obtained was examined for its enzymological properties. The enzyme activity was determined basically by adding the substrate N-benzyl-3-pyrrolidinone (1 mM), the coenzyme NADPH (0.167 mM) and the enzyme to 100 mM phosphate buffer (pH 6.5), allowing the reaction to proceed at 30° C. for 1 minute and measuring the decrease in absorbance at the wavelength 340 nm.

(1) Action:

It acted on N-benzyl-3-pyrrolidinone with NADPH as the coenzyme and produced (S)-N-benzyl-3-pyrrolidinol with an optical purity of not less than 99% ee.

(2) Optimum Action pH:

The enzyme activity was measured by the above method within the pH range of 4.0 to 7.0 using phosphate buffer and acetate buffer as a buffer. As a result, the optimum pH for the action on N-benzyl-3-pyrrolidinone was found to be 4.5 to 5.5.

(3) Optimum Action Temperature:

The enzyme activity against the substrate N-benzyl-3-pyrroiidinone exerted for one minute of the reaction was measured within the temperature range of 20° C. to 60° C. As a result, the optimum temperature was found to be 40° C. to 45° C.

(4) Molecular Weight:

The molecular weight of this enzyme was determined by gel filtration using a TSK-GEL G3000 SWXL column (product of Tosoh) and, as the eluent, 100 mM phosphate buffer (pH 7.0) containing 5 mM 2-mercaptoethanol and 100 mM sodium sulfate. The molecular weight of the subunit of the enzyme was calculated from the relative mobility relative to reference proteins in SDS-polyacrylamide gel electrophoresis. As a result, the molecular weight of the enzyme was found to be about 29,000 as determined by gel filtration analysis or about 35,000 as determined by SDS-polyacrylamide gel electrophoretic analysis.

(5) Inhibitors:

The reaction was repeated with the addition of various metal ions and inhibitors shown in Table 1 and, with the activity without addition being taken as 100%, the relative activities upon addition thereof were examined. As shown in Table 1, the enzyme was inhibited by the divalent copper ion.

TABLE 1

| Compound | Addition level (mM) | Relative activity (%) |
|---|---|---|
| None | — | 100 |
| $CoCl_2$ | 1 | 99 |
| $CuSO_4$ | 0.1 | 6 |
|  | 1 | 5 |
| $ZnSO_4$ | 1 | 99 |
| $MnCl_2$ | 1 | 89 |
| $MgSO_4$ | 1 | 99 |
| 1,10-Phenanthroline | 1 | 90 |
| 5,5-Diphenylhydantoin | 0.5 | 99 |
| EDTA | 1 | 88 |
| PMSF | 1 | 89 |

TABLE 1-continued

| Compound | Addition level (mM) | Relative activity (%) |
|---|---|---|
| PCMB | 0.1 | 78 |
| DTNB | 0.01 | 93 |
| Iodoacetic acid | 1 | 89 |
| NEM | 1 | 94 |
| Quercetin | 0.01 | 94 |

EXAMPLE 3

Cloning of BRD Gene (Preparation of Synthetic Oligonucleotide Probes)

The purified BRD obtained in Example 1 was digested with bovine pancreas-derived trypsin (product of Wako Pure Chemical Industries), and the amino acid sequences of peptide fragments obtained were determined using ABI 492 model protein sequencer (product of Perkin Elmer). Based on this amino acid sequence, two DNA primers shown under SEQ ID NO:3 and SEQ ID NO:4 in the sequence listing were synthesized in the conventional manner.

(Amplification of BRD Gene by PCR)

The chromosomal DNA was extracted from cultured cells of the strain *Micrococcus luteus* IFO 13867 by the method of Murray et al. (Nucl., Acids Res. 8:4321–4325 (1980)). Then, using the DNA primers prepared as mentioned above, PCR was carried out with the chromosomal DNA obtained as the template, whereupon a DNA fragment (about 250 bp) supposed to be part of the BRD gene was amplified.

(Construction of Chromosomal DNA Library)

The chromosomal DNA of the strain *Micrococcus luteus* IFO 13867 was completely digested with the restriction enzyme BamHI, followed by separation by agarose gel electrophoresis. Then, using the DNA fragment obtained in the above manner (about 250 bp) as the probe, the digest of the chromosomal DNA was analyzed by the Southern method (J. Mol. Biol., 98, 503 (1975)) (the labeling of the DNA probe and detection thereof being carried out using the Gene Images labeling/detection system (product of Amersham)). As a result, a DNA fragment of about 4.5 kb was found to hybridize with the above DNA probe.

Therefore, the above digest was subjected to separation by agarose gel electrophoresis, and 4.3 kb to 6.2 kb DNA fragments were recovered. These DNA fragments were inserted into the vector plasmid pUC19 (product of Takara Shuzo) at the BamHI site thereof, followed by introduction into the strain *Escherichia coli* JM109 (product of Takara Shuzo). A chromosomal DNA library of this strain was thus constructed.

(Screening of the Chromosomal DNA Library)

Using the DNA fragment obtained in the above manner as the probe, the chromosomal DNA library constructed in the above manner was subjected to screening by the colony hybridization method (the labeling of the DNA probe and detection thereof being carried out using the Gene Images labeling/detection system (product of Amersham) and the experimental procedure being performed according to the manual attached to the system). As a result, one positive colony was obtained. Therefore, a recombinant plasmid pUC-BB, produced by insertion of the DNA (about 4.5 kb) obtained from this positive colony was selected as a BRD gene-containing chromosomal DNA clone.

(Determination of Nucleotide Sequence)

The recombinant plasmid pUC-BB obtained in the above manner was treated with various restriction enzymes and the resulting digestion fragments were analyzed, and a restriction enzyme cleavage map thereof was prepared. Then, recombinant plasmids were constructed by inserting various DNA fragments obtained on the occasion of the above analysis into pUC19 at the multicloning site thereof. Using these recombinant plasmids, the nucleotide sequences of each inserted fragment was analyzed using an ABI PRISM Dye Terminator Cycle Sequencing Ready Reaction Kit (product of Perkin Elmer) and ABI 373A DNA Sequencer (product of Perkin Elmer), and the nucleotide sequence of a DNA fragment (about 1.4 kb) supposed to contain the target gene was determined. That nucleotide sequence is shown in FIG. 1. As for the structural gene portion in this nucleotide sequence, the amino acid sequence deduced from that nucleotide sequence is shown below the nucleotide sequence in FIG. 1. As a result of comparison of this amino acid sequence with the partial amino acid sequence of digested fragments of purified BRD by trypsin, the whole partial amino acid sequence of purified BRD was found to exist in the amino acid sequence deduced from the nucleotide sequence and to be quite identical in that portion (the underlined amino acid sequence in FIG. 1). Thus, that gene was judged to be the BRD gene.

EXAMPLE 4

Construction of BRD Gene-containing Recombinant Plasmid

A double-stranded DNA resulting from addition of an NdeI site to the initiation codon portion of the structural gene of BRD and further addition, just behind the 3' terminus thereof, of a termination codon (TAA) and an EcoRI cleavage point was obtained in the following manner. Based on the nucleotide sequence determined in Example 3, an N-terminal DNA primer with an NdeI site added to the initiation codon part of the BRD gene and a C-terminal DNA primer with a termination codon (TAA) and an EcoRI site added just behind the 3' terminus of the same gene were synthesized. The nucleotide sequences of these two primers are shown under SEQ ID NO:5 and SEQ ID NO:6 in the sequence listing. Using these two synthetic DNA primers, together with the plasmid pUC-BB obtained in Example 3 as the template, a double-stranded DNA was amplified by PCR. The DNA fragment obtained was digested with NdeI and EcoRI, and the resulting fragment was inserted into the plasmid pUCNT (WO 94/03613) at the NdeI-EcoRI site downstream of the lac promoter to give a recombinant plasmid pNTBR.

EXAMPLE 5

Addition of Shine-Dalgarno Sequence to a Site Upstream of the BRD Gene

For attaining high level expression of the BRD gene in *Escherichia coli*, a plasmid was obtained from the plasmid pNTBR prepared in Example 4 by newly adding the *E.coli*-derived Shine-Dalgarno sequence (9 bases) to a site upstream of the initiation codon of the same gene, as follows. First, a plasmid pUCT was constructed by converting G in the NdeI site of the *E.coli* expression vector pUCNT used in Example 4 to T by the PCR method. Then, an N-terminal DNA primer resulting from addition of the *E.coli*-derived Shine-Dalgarno sequence (9 bases) at 5 bases upstream of the initiation codon of the BRD gene shown under SEQ ID NO:2 in the sequence listing and further addition of an EcoRI site at just before the Shine-Dalgarno sequence and a C-terminal DNA primer resulting from addition of a SacI site just behind the 3' terminus of the same gene were synthesized in the conventional manner. The nucleotide sequences of these two primers are shown under SEQ ID NO:7 and SEQ ID NO:8 in the sequence listing. Using these two DNA primers, with the plasmid pNTBR constructed in Example 4 as the template, a double-stranded DNA was synthesized by PCR. The DNA fragment obtained was digested with EcoRI and SacI, and the resulting fragment was inserted into the plasmid pUCT at the EcoRI-SacI site (downstream of the lac promoter) to give a recombinant plasmid pTBH.

EXAMPLE 6

Reduction in GC Ratio in BRD Gene

For further attaining high level expression of the BRD gene in *E.coli*, a plasmid pTSBH was constructed by substituting a DNA lower in GC ratio for the segment from the 1st to 118th base of the same gene in the plasmid pTBH constructed in Example 5, without altering the amino acid sequence coded thereby, as follows.

A double-stranded DNA having the sequence shown under SEQ ID NO:9 in the sequence listing was prepared by the conventional method. This was digested with EcoRI and XhoI, and a plasmid pTSBH substituted for the DNA fragment detached from pTBH by digestion with the same restriction enzymes and containing a 5' terminal portion of the BRD gene was obtained.

EXAMPLE 7

Construction of Recombinant Plasmid Containing both BRD Gene and Glucose Dehydrogenase Gene A double-stranded DNA resulting from addition of the *E.coli*-derived Shine-Dalgarno sequence (9 bases) at 5 bases upstream of the initiation codon of the strain *Bacillus megaterium* IAM 1030-derived glucose dehydrogenase (hereinafter referred to as GDH) gene, of a SacI cleavage point just before the above sequence and of a BamHI cleavage point just behind the termination codon was prepared in the following manner. Based on the nucleotide sequence information about the GDH gene, an N-terminal DNA primer resulting from addition of the *E.coli*-derived Shine-Dalgarno sequence (9 bases) at 5 bases upstream of the initiation codon of the structural gene of GDH and further addition of a SacI cleavage point just before the above sequence, and a C-terminal DNA primer resulting from addition of a BamHI site just behind the termination codon of the structural gene of GDH were synthesized by the conventional method. The nucleotide sequences of these two primers are shown under SEQ ID NO:10 and SEQ ID NO:11, respectively, in the sequence listing. Using these two DNA primers, together with the plasmid pGDK1 (Eur. J. Biochem. 186, 389 (1989)) as the template, a double-stranded DNA was synthesized by PCR. The DNA fragment obtained was digested with SacI and BamHI and inserted into the SacI-BamHI site (occurring downstream of the BRD gene) of the pTSBH constructed in Example 5 to give a recombinant plasmid pTSBG1. The method of constructing pTSBG1 and the structure thereof are shown in FIG. 2.

EXAMPLE 8

Production of Recombinant *E.coli*

*E.coli* HB101 (product of Takara Shuzo) was transformed using the recombinant plasmids pTBH, pSTBH and pTSBG1 obtained in Examples 5, 6 and 7, to give recombinant *E.coli* HB101 (pTBH), HB101 (pTSBH) and HB101 (pTSBG1), respectively. Among the thus-obtained transformants, *E.coli* HB101 (pTSBH) and HB101 (pTSBG1) have been deposited with the National Institute of Advanced Industrial Science and Technology International Patent Organism Depositary (Address: Central 6, 1-1 Higashi 1-chome, Tsukuba City, Ibaraki Prefecture, Japan) under the accession number FERM BP-7118 (deposition date: Apr. 11, 2000) and the accession number FERM BP-7119 (deposition date: Apr. 11, 2000), respectively.

Further, the plasmid pGDA2 (J. Biol. Chem., (1989), 264, 6381) was double-digested with EcoRI and PstI and the thus-obtained DNA fragment (about 0.9 kb) containing the *Bacillus megaterium* IWG3-derived GDH gene was inserted into the plasmid pSTV28 (product of Takara Shuzo) at the EcoRI-PstI site thereof to construct a recombinant plasmid pSTVG. *E.coli* HB101 (pTSBH) made competent in advance by the calcium chloride method was transformed with this plasmid pSTVG at a high rate of introduction. Thus, *E.coli* HB101 (pTSBH, pSTVG) was obtained with ease.

EXAMPLE 9

BRD Expression in Recombinant *E.coli*

The recombinants *E.coli* HB101 (pTBH) and HB101 (PTSBH) obtained in Example 8 were each shake-cultured on 2×YT medium containing 200 g/ml of ampicillin at 28° C. for 15 hours. A 1-ml portion of this preculture fluid was inoculated into 100 ml of a medium sterilized by autoclaving in a 500-ml Sakaguchi flask and comprising 1.5% (w/v) glycerol, 1.5% (w/v) Bacto tryptone, 0.4% (w/v) Bacto yeast extract, 0.2% (w/v) sodium chloride, 0.8% (w/v) potassium dihydrogen Phosphate, 0.05% (w/v) magnesium sulfate heptahydrate and 0.033% (w/v) Adekanol LG109 (product of Asahi Denka Kogyo), as adjusted to pH 6.0, and shake culture was carried out at 30° C. for 60 hours. Cells were harvested from such culture fluids by using a centrifuge, then suspended in 100 mM phosphate buffer (pH 6.5) and untrasonically disrupted to give a cell-free exract.

The BRD activity of this cell-free extract was determined in the following manner. Thus, the BRD activity was determined by adding the substrate N-benzyl-3-pyrrolidinone (1 mM), the coenzyme NADPH (0.167 mM) and the enzyme to 100 mM phosphate buffer (pH 6.5) and measuring the decrease in absorbance at the wavelength 340 nm at 30° C. The enzyme activity capable of oxidizing 1 μmol of NADPH to NADP in 1 minute under these reaction conditions was defined as 1 unit. Thus-determined BRD activities of the cell-free extracts were expressed in terms of specific activity and compared with that of the transformant holding the vector plasmid pUCNT. Comparison was also made with the BRD activity of a cell-free extract derived from the strain *Micrococcus luteus* IFO 13867 as prepared in the same manner as in Example 1. The results thus obtained are shown in Table 2.

TABLE 2

| Name of strain | Specific BRD activity (U/mg) |
| --- | --- |
| E. coli HB101(pUCNT) | <0.01 |
| E. coli HB101(pTBH) | 0.06 |
| E. coli HB101(pTSBH) | 0.61 |
| Micrococcus luteus IFO 13867 | 0.06 |

As for E.coli HB101 (pTSBH), a distinct increase in BRD activity was observed as compared with E.coli HB101 (pUCNT) which is transformed with the vector plasmid alone and, when compared with the strain Micrococcus luteus IFO 13867, the activity was about 10-fold higher.

EXAMPLE 10

Simultaneous Expression of BRD and GDH in Recombinant E.coli

The recombinant E.coli HB101 (pTSBG1) and HB101 (pTSBH, pSTVG) obtained in Example 8 were cultured and treated in the same manner as in Example 9 to give the respective cell-free extracts, which were assayed for GDH activity in the following manner. The GDH activity was determined by adding the substrate glucose (0.1 M), the coenzyme NADP (2 mM) and the enzyme to 1 M Tris hydrochloride buffer (pH 8.0) and measuring the increase in absorbance at the wavelength 340 nm at 25° C. The enzyme activity capable of reducing 1 µmol of NADP to NADPH in 1 minute under these reaction conditions was defined as 1 unit. The BRD activity was also determined in the same manner as in Example 9. Thus-determined BRD and GDH activities of the cell-free extracts were each expressed in terms of specific activity and compared with those of E.coli HB101 (pTSBH) and HB101 (pUCNT) which is transformed with the vector alone. The results are shown in Table 3.

TABLE 3

| Name of strain | Specific BRD activity (U/mg) | Specific GDH activity (U/mg) |
| --- | --- | --- |
| E. coli HB101(pUCNT) | <0.01 | <0.01 |
| E. coli HB101(pTSBH) | 0.61 | <0.01 |
| E. coli HB101(pTSBG1) | 0.52 | 89 |
| E. coli HB101(pTSBH, pSTVG) | 0.69 | 3.2 |

As for E.coli HB101 (pTSBG1) and HB101 (pTSBH, pSTVG), distinct increases in BRD activity and GDH activity were observed as compared with E.coli HB101 (pUCNT) which is transformed with the vector plasmid alone.

EXAMPLE 11

Synthesis of (S)-N-benzyl-3-pyrrolidinol from N-benzyl-3-pyrrolidinone using Recombinant E.coli Produced by Introduction of BRD Gene The culture fluid of the recombinant E.coli HB101 (pTSBH) obtained in Example 9 was ultrasonically disrupted using SONIFIRE 250 (product of BRANSON). To 25 ml of this cell disruption fluid were added 1,350 U of glucose dehydrogenase (product of Amano Pharmaceutical), 3.0 g of glucose, 3.0 mg of NADP and 0.25 g of N-benzyl-3-pyrrolidinone. While this reaction mixture was stirred at 30° C. with pH adjusted to 6.5 using 5 M hydrochloric acid or sodium hydroxide, N-benzyl-3-pyrrolidinone was added thereto at an interval of 0.25 g/hour. After addition of a total of 2.0 g of N-benzyl-3-pyrrolidinone, stirring was further continued for 20 hours. After completion of the reaction, 2.5 ml of a 5 M aqueous solution of sodium hydroxide was added, the mixture was extracted with toluene, and the solvent was removed. Analysis of the resulting extract revealed that N-benzyl-3-pyrrolidinol was obtained in 74% yield. The N-benzyl-3-pyrrolidinol produced on that occasion was the S form with an optical purity of not less than 99% ee.

The quantity of N-benzyl-3-pyrrolidinone and N-benzyl-3-pyrrolidinol was determined by gas chromatography (column: Uniport B 10% PEG-20 M (3.0 mm ID×1.0 m), column temperature: 200° C., carrier gas: nitrogen, detection: FID). The optical purity of (S)-N-benzyl-3-pyrrolidinol was determined by high performance liquid chromatography (column: Chiralcel OB (product of Daicel Chemical Industries), eluent: n-hexane/isopropanol/diethylamine=950/50/1, flow rate: 1 ml/min, detection: 254 nm).

EXAMPLE 12

Synthesis of (S)-N-benzyl-3-pyrrolidinol from N-benzyl-3-pyrrolidinone using Recombinant E.coli Capable of Simultaneous Expression of BRD and Glucose Dehydrogenase To 25 ml of the culture fluid of the recombinant E.coli HB101 (pTSBG1) obtained in Example 9 were added 2.5 g of glucose, 3.0 mg of NADP and 0.25 g of N-benzyl-3-pyrrolidinone. While this reaction mixture was stirred at 30° C. with pH adjusted to 6.5 using 5 M hydrochloric acid or sodium hydroxide, N-benzyl-3-pyrrolidinone was added thereto at an interval of 0.25 g/2 hours. After addition of a total of 1.0 g of N-benzyl-3-pyrrolidinone, stirring was further continued for 17 hours. After completion of the reaction, 1.2 ml of a 5 M aqueous solution of sodium hydroxide was added, the mixture was extracted with toluene, and the solvent was removed. Analysis of the resulting extract revealed that N-benzyl-3-pyrrolidinol was obtained in 92% yield. The N-benzyl-3-pyrrolidinol produced on that occasion was the S form with an optical purity of not less than 99% ee.

EXAMPLE 13

Synthesis of (S)-N-benzyl-3-pyrrolidinol from N-benzyl-3-pyrrolidinone using Recombinant E.coli Capable of Simultaneous Expression of BRD and Glucose Dehydrogenase To 25 ml of the culture fluid of the recombinant E.coli HB101 (pTSBH, pSTVG) obtained in Example 9 were added 2.5 g of glucose, 3.0 mg of NADP and 0.25 g of N-benzyl-3-pyrrolidinone. While this reaction mixture was stirred at 30° C. with pH adjusted to 6.5 using 5 M hydrochloric acid or sodium hydroxide, N-benzyl-3-pyrrolidinone was added thereto at an interval of 0.25 g/hour. After addition of a total of 2.0 g of N-benzyl- 3-pyrrolidinone, stirring was further continued for 16 hours. After completion of the reaction, 2.5 ml of a 5 M aqueous solution of sodium hydroxide was added, the mixture was extracted with toluene, and the solvent was removed. Analysis of the resulting extract revealed that N-benzyl-3-pyrrolidinol was obtained in 93% yield. The N-benzyl-3-pyrrolidinol produced on that occasion was the S form with an optical purity of not less than 99% ee.

INDUSTRIAL APPLICABILITY

As a result of cloning of a gene of a polypeptide having enzyme activity in asymmetrically reducing N-benzyl-3-pyrrolidinone to produce (S)-N-benzyl-3-pyrrolidinol and analysis of the nucleotide sequence thereof, it has become possible to obtain a transformant capable of producing, at high levels, the above polypeptide. It has also become possible to obtain a transformant capable of producing, at high levels, the polypeptide and glucose dehydrogenase simultaneously. Furthermore, it has become possible to efficiently synthesize (S)-N-benzyl-3-pyrrolidinol from N-benzyl-3-pyrrolidinone using such transformants.

The invention claimed is:

1. An isolated and purified DNA molecule encoding a polypeptide comprising SEQ ID NO: 1.

2. An isolated and purified DNA molecule encoding a polypeptide wherein the polypeptide comprises the enzyme activity of asymmetrically reducing N-benzyl-3-pyrrolidinone into (S)-N-benzyl-3-pyrrolidinol, and wherein the DNA molecule hybridizes to SEQ ID NO: 2 under stringent conditions at 65° C. in the presence of 0.7 to 1.0 M NaCl.

3. An expression vector comprising the isolated DNA molecule of claim 1.

4. The expression vector of claim 3, wherein the vector is a plasmid pTSBH.

5. The expression vector of claim 3, which further comprises an isolated DNA molecule encoding a polypeptide having glucose dehydrogenase activity.

6. The expression vector of claim 5, wherein the polypeptide having glucose dehydrogenase activity is a *Bacillus megaterium*-derived glucose dehydrogenase.

7. The expression vector of claim 6, wherein the vector is a plasmid pTSBG1.

8. An isolated host cell transformed with the expression vector of claim 3.

9. An isolated host cell transformed with both the expression vector of claim 3 and an expression vector comprising a DNA molecule encoding a polypeptide having glucose dehydrogenase activity.

10. The transformant of claim 9, wherein the polypeptide having glucose dehydrogenase activity is a *Bacillus megaterium*-derived glucose dehydrogenase.

11. The transformant of claim 8, wherein the host is *Escherichia coli*.

12. The transformant of claim 11, wherein the transformant is *Escherichia coli* HB101 (pTSBH) obtained by transforming *Escherichia coli* using the recombinant plasmid pTSBH.

13. An isolated transformed host cell, wherein the transformant is *Escherichia coli* HB101 (pTSBG1) obtained by transforming *Escherichia coli* HB101 using the recombinant plasmid pTSBG 1.

14. The transformant of claim 9, wherein the transformant is *Escherichia coli* HB101 (pTSBH, pSTVG) obtained by transforming *Escherichia coli* HB101 using both the recombinant plasmid pTSBH and the recombinant plasmid pSTVG.

15. A method of producing (S)-N-benzyl-3-pyrrolidinol comprising:
    a) culturing the transformant of claim 8 in presence of N-benzyl-3-pyrrolidinone, and
    b) harvesting the (S)-N-benzyl-3-pyrrolidinol produced in a).

16. The method of claim 15, wherein step (a) is carried out in the presence of a coenzyme regenerating system.

17. An expression vector comprising the isolated DNA-molecule of claim 2.

18. An isolated and purified polypeptide encoded by the DNA molecule of claim 1.

19. An isolated and purified polypeptide encoded by the DNA molecule of claim 2, wherein said polypeptide comprises the enzyme activity of asymmetrically reducing N-benzyl-3-pyrrolidinone into (S)-N-benzyl-3-pyrrolidinol.

* * * * *

SEQUENCE LISTING

```
<160> NUMBER OF SEQ ID NOS: 11

<210> SEQ ID NO 1
<211> LENGTH: 277
<212> TYPE: PRT
<213> ORGANISM: Micrococcus luteus

<400> SEQUENCE: 1

Met Arg Arg Met Thr Leu Pro Ser Gly Glu Ser Ile Pro Val Leu Gly
 1               5                  10                  15

Gln Gly Thr Trp Gly Trp Gly Glu Asp Pro Gly Arg Arg Gly Asp Glu
            20                  25                  30

Val Ala Ala Leu His Ala Gly Leu Glu Leu Gly Met Thr Leu Val Asp
        35                  40                  45

Thr Ala Glu Met Tyr Ala Asp Gly Gly Ala Glu Val Ala Gly Glu
    50                  55                  60

Ala Leu Ala Gly Arg Arg Asp Glu Ala Phe Val Val Ser Lys Val Met
65                  70                  75                  80

Pro Ser His Ala Ser Arg Ser Gly Thr Ile Ala Ala Cys Glu Arg Ser
                85                  90                  95

Leu Lys Arg Leu Gly Thr Asp Arg Ile Asp Leu Tyr Leu Leu His Trp
            100                 105                 110

Gln Gly Arg Tyr Pro Leu Gln Asp Thr Val Ala Ala Phe His Gln Leu
        115                 120                 125

Val Glu Asp Gly Lys Ile Arg Tyr Trp Gly Val Ser Asn Phe Asp His
    130                 135                 140

Arg Ala Leu Ala Glu Leu Gln Asp Val Pro Gly Thr Ser Gly Leu Thr
145                 150                 155                 160

Thr Asp Gln Val Leu Tyr Asn Leu Ser Arg Arg Gly Pro Glu Tyr Asp
                165                 170                 175

Leu Leu Pro Trp Cys Ala Asp His Gln Leu Pro Val Met Ala Tyr Ser
            180                 185                 190

Pro Ile Glu Gln Gly Arg Ile Leu Asp Asp Thr Thr Leu Asn Asp Val
        195                 200                 205

Ala Ala Arg His Ser Val Ser Pro Ala Ala Ala Leu Ala Trp Val
    210                 215                 220

Leu Arg Arg Asp Ser Leu Cys Thr Ile Pro Lys Ala Ser Ser Pro Gln
225                 230                 235                 240

His Val Arg Asp Asn Ala Thr Ala Leu Asp Val Glu Leu Thr Arg Glu
                245                 250                 255

Asp Leu Asp Ala Leu Asp Arg Ala Phe Pro Pro Ser Gly Pro Arg
            260                 265                 270

Pro Leu Glu Met Leu
        275
```

<210> SEQ ID NO 2
<211> LENGTH: 1410
<212> TYPE: DNA
<213> ORGANISM: Micrococcus luteus
<220> FEATURE:
<221> NAME/KEY: CDS
<222> LOCATION: (108)..(938)

<400> SEQUENCE: 2

```
ggtacccgcc gccctcctat aagccagcac cggtcgagga cgcgccggcc cttcgaggat       60
ctcagcccac gtcccgcctc aggacaacca gaaggaagtg atcgcgg atg cga cgg       116
                                                    Met Arg Arg
                                                      1 atg acg ctg ccg agt ggg gag tcc atc cct gtg ctg ggc cag ggc acc       164
Met Thr Leu Pro Ser Gly Glu Ser Ile Pro Val Leu Gly Gln Gly Thr
      5                  10                  15 tgg ggc tgg ggt gag gac ccc ggc cgc cgc ggc gac gag gtc gcc gcg       212
Trp Gly Trp Gly Glu Asp Pro Gly Arg Arg Gly Asp Glu Val Ala Ala
 20                  25                  30                  35 ctg cac gcc ggc ctc gag ctg ggc atg acg ctg gtc gac acc gcc gag       260
Leu His Ala Gly Leu Glu Leu Gly Met Thr Leu Val Asp Thr Ala Glu
                 40                  45                  50 atg tac gcc gac ggc ggt gcg gag gag gtg gct ggt gaa gca ttg gcg       308
Met Tyr Ala Asp Gly Gly Ala Glu Glu Val Ala Gly Glu Ala Leu Ala
             55                  60                  65 ggt cgc cgc gac gag gcg ttc gtg gtc agc aag gtc atg ccg tcc cac       356
Gly Arg Arg Asp Glu Ala Phe Val Val Ser Lys Val Met Pro Ser His
         70                  75                  80 gcc tcc cgt tcc ggc acg atc gcg gcc tgc gaa cgc agc ctg aaa cgc       404
Ala Ser Arg Ser Gly Thr Ile Ala Ala Cys Glu Arg Ser Leu Lys Arg
 85                  90                  95 ctg ggc acc gat cgg atc gac ctc tac ctg ctg cac tgg cag ggc agg       452
Leu Gly Thr Asp Arg Ile Asp Leu Tyr Leu Leu His Trp Gln Gly Arg
100                 105                 110                 115 tac ccg ctg cag gac acc gtc gcg gcc ttc cac cag ctc gtc gag gac       500
Tyr Pro Leu Gln Asp Thr Val Ala Ala Phe His Gln Leu Val Glu Asp
                120                 125                 130 ggg aaa atc cga tac tgg ggc gtc agc aac ttc gac cac cgg gcc ctc       548
Gly Lys Ile Arg Tyr Trp Gly Val Ser Asn Phe Asp His Arg Ala Leu
            135                 140                 145 gcc gag ctg cag gac gtg ccg ggc acc agc ggg ctg acc acg gat cag       596
Ala Glu Leu Gln Asp Val Pro Gly Thr Ser Gly Leu Thr Thr Asp Gln
        150                 155                 160 gtg ctg tac aac ctg tcg cgg cga gga ccg gag tac gac ctg ctg ccg       644
Val Leu Tyr Asn Leu Ser Arg Arg Gly Pro Glu Tyr Asp Leu Leu Pro
165                 170                 175 tgg tgc gcc gac cac cag ctg ccg gtc atg gcg tac tcg ccg atc gag       692
Trp Cys Ala Asp His Gln Leu Pro Val Met Ala Tyr Ser Pro Ile Glu
180                 185                 190                 195 cag ggc cgc atc ctt gac gac acg acg ctg aac gac gtc gcg gcc cgt       740
Gln Gly Arg Ile Leu Asp Asp Thr Thr Leu Asn Asp Val Ala Ala Arg
                200                 205                 210 cac agc gtc agc ccc gcg gcg gcg gcc ctt gcc tgg gtg ctg cgc cgc       788
His Ser Val Ser Pro Ala Ala Ala Ala Leu Ala Trp Val Leu Arg Arg
            215                 220                 225 gac tcg ctc tgc acg atc ccc aag gcg agc agc ccg cag cac gtg cgc       836
Asp Ser Leu Cys Thr Ile Pro Lys Ala Ser Ser Pro Gln His Val Arg
        230                 235                 240 gac aac gcc aca gca ctg gac gtg gag ctg acc cgc gaa gac ctg gat       884
Asp Asn Ala Thr Ala Leu Asp Val Glu Leu Thr Arg Glu Asp Leu Asp
```

-continued

```
                        245                 250                 255
gct ctg gac cgt gcg ttt ccg ccc ccg agc gga ccg cga cca ctg gaa         932
Ala Leu Asp Arg Ala Phe Pro Pro Pro Ser Gly Pro Arg Pro Leu Glu
260                 265                 270                 275 atg ctg tgaccctgcc ccagggcgca gcccggtcgg tccgggcggt ccgggcagtc          988
Met Leu cgggcagcgc tccggtcagc gcaagtctcc gaaggacctg cctgtcacct cctcctgaac      1048
ctgtgcacgc catccatcga ctcctttcct cgagccctgt cgggttcgcg gtaggcgctg      1108
atcatccgct ggcaggtccc ccaagtggcc tcgagccggg ccctctgctt gtcggtgagc      1168
aacccggttc cggcgtgcag ggttcgacgg gcggagtaga gcgggtcgcc cgtgcggccg      1228
cggtggccat gcaggtcctg ctggacccgg cggtggcagc ggaccaacgc gtcgccggct      1288
aaccggactg cgagcgaccg gcgttgtgga cgcagacgac ctggacactg ggccgtgcgg      1348
tcaggaggat ctccaaagtc ggcggcgggg gttcaggcga tgtcgaggaa ggaacggagc      1408
tc                                                                     1410
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: a, t, c, g, other or unknown
<220> FEATURE:
<221> NAME/KEY: modified_base
<222> LOCATION: (9)
<223> OTHER INFORMATION: a, t, c, g, other or unknown

<400> SEQUENCE: 3
gayacngcng aratgtaygc                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: a, t, c, g, other or unknown
<220> FEATURE:
<221> NAME/KEY: modified_base
<222> LOCATION: (9)
<223> OTHER INFORMATION: a, t, c, g, other or unknown

<400> SEQUENCE: 4
tcytcnacna gytgrtgraa                                                    20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 5
gcgcatatgc gacggatgac gctgcc                                             26

<210> SEQ ID NO 6
```

```
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
ggcgaattct tacagcattt ccagtggtcg cg                              32

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 7
gcgaattcta aggagattta tatatgcgac ggatgacgct gccgag              46

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
caggagctct tacagcattt ccagtggtc                                 29

<210> SEQ ID NO 9
<211> LENGTH: 144
<212> TYPE: DNA
<213> ORGANISM: Artificial Sequence
<220> FEATURE:
<223> OTHER INFORMATION: Description of Artificial Sequence: Synthetic
       double-stranded DNA

<400> SEQUENCE: 9
gaattctaag gagatttaca tatgcgtcgt atgactttac catctggtga atctattcca    60
gttttaggtc aaggtacttg gggttggggt gaagatccag gtcgtcgtgg tgatgaagtt   120
gctgctttac atgctggtct cgag                                         144

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 10
caggagctct aaggaggtta acaatgtata aag                            33

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 11
cacggatcct tatccgcgtc ctgcttgg                                  28
```